(12) United States Patent
Ehrlich (10) Patent No.: US 12,087,115 B2
(45) Date of Patent: Sep. 10, 2024

(54) SYSTEMS AND METHODS OF ACCESS CONTROL WITH HAND SANITATION

(71) Applicant: Tyco Fire & Security GmbH, Neuhausen am Rheinfall (CH)

(72) Inventor: Alexis B. Ehrlich, Boca Raton, FL (US)

(73) Assignee: Tyco Fire & Security GmbH, Neuhausen am Rheinfall (CH)

( * ) Notice: Subject to any disclaimer, the term of this patent is extended or adjusted under 35 U.S.C. 154(b) by 0 days.

(21) Appl. No.: 17/215,703

(22) Filed: Mar. 29, 2021

(65) Prior Publication Data

US 2022/0309854 A1    Sep. 29, 2022

(51) Int. Cl.
   *G07C 9/22*    (2020.01)
   *A61L 2/10*    (2006.01)
   *G07C 9/27*    (2020.01)
   *G08B 21/24*   (2006.01)

(52) U.S. Cl.
   CPC .................. *G07C 9/22* (2020.01); *A61L 2/10* (2013.01); *G07C 9/27* (2020.01); *G08B 21/245* (2013.01)

(58) Field of Classification Search
   CPC ........ G07C 9/22; G07C 9/27; G07C 9/00563; A61L 2/10; A61L 2/26; A61L 2202/11; G08B 21/245; G06F 17/18
   See application file for complete search history.

(56) References Cited

U.S. PATENT DOCUMENTS

| | | | | |
|---|---|---|---|---|
| 5,900,067 | A * | 5/1999 | Jones ................. | G01N 21/6447 252/301.16 |
| 2009/0195385 | A1* | 8/2009 | Huang ................... | G16H 40/20 340/572.1 |
| 2019/0354753 | A1* | 11/2019 | Worrall ................ | G09B 19/003 |
| 2021/0335072 | A1* | 10/2021 | Caldwell ............ | G07C 9/00563 |

* cited by examiner

*Primary Examiner* — Vernal U Brown
(74) *Attorney, Agent, or Firm* — ARENTFOX SCHIFF LLP (57) ABSTRACT

Example aspects include a method, an apparatus and a computer-readable medium of operating an access control system, comprising detecting whether a person has sanitized one or more body parts of the person. The aspects further include obtaining, in response to detecting that the person has sanitized the one or more body parts, access credentials of the person. Additionally, the aspects further include determining whether to grant access to the person based at least on the access credentials and detecting that the person has sanitized the one or more body parts.

21 Claims, 6 Drawing Sheets

SYSTEMS AND METHODS OF ACCESS CONTROL WITH HAND SANITATION

BACKGROUND

Technical Field

The present disclosure relates generally to access control systems, and more particularly, to systems and methods for access control based on hand sanitation.

INTRODUCTION

Access control systems may be used to selectively provide people with access to specific locations in a building and/or facility. The access control systems may provide access by permitting a person to pass through a checkpoint, such as a door, a gate, a turnstile, an elevator, an identification checkpoint, and/or other impediments. For example, the access control systems may require the person to present access credentials in order to obtain permission to pass through the checkpoint to enter and/or exit one or more secured areas. The access control systems may comprise keypads, card readers, key fob readers, cameras, biometric sensors, beacons, and/or other devices to receive the access credentials. The access control systems may determine whether or not to permit the person to access the one or more secured areas based on the received access credentials. Typically, the person may need to touch a device of the access control system in order to present the access credentials, such as scanning an identification card, entering a code on a keypad, and/or touching a fingerprint sensor. In addition, the person may need to touch portions of the checkpoint in order to pass through the checkpoint, such as pulling on a door handle, turning a door knob, pushing a turnstile, and the like.

These physical procedures for presenting the access credentials and/or passing through the checkpoint may not be desirable during an epidemic or pandemic, as these physical procedures may facilitate the spread of a contagious disease (e.g., COVID-19). However, conventional access control systems may not provide solutions for detecting that the person has sanitized one or more body parts (e.g., hands and/or palms) prior to performing these physical procedures. Thus, there exists a need for further improvements to access control systems. Improvements are presented herein. These improvements may also be applicable to other systems that employ access control techniques.

SUMMARY

The following presents a simplified summary of one or more aspects in order to provide a basic understanding of such aspects. This summary is not an extensive overview of all contemplated aspects, and is intended to neither identify key or critical elements of all aspects nor delineate the scope of any or all aspects. Its sole purpose is to present some concepts of one or more aspects in a simplified form as a prelude to the more detailed description that is presented later.

An example aspect includes a method of operating an access control system, comprising detecting whether a person has sanitized one or more body parts of the person. The method further includes obtaining, in response to detecting that the person has sanitized the one or more body parts, access credentials of the person. Additionally, the method further includes determining whether to grant access to the person based at least on the access credentials and detecting that the person has sanitized the one or more body parts.

Another example aspect includes an apparatus of an access control system, comprising a non-transitory memory storing computer-executable instructions and a processor communicatively coupled with the non-transitory memory. The processor is configured to execute the computer-executable instructions to detect whether a person has sanitized one or more body parts of the person. The processor is further configured to obtain, in response to detecting that the person has sanitized the one or more body parts, access credentials of the person. Additionally, the processor is further configured to execute further instructions to determine whether to grant access to the person based at least on the access credentials and detecting that the person has sanitized the one or more body parts.

Another example aspect includes a non-transitory computer-readable medium storing computer-readable instructions for operating an access control system, executable by a processor to detect whether a person has sanitized one or more body parts of the person. The instructions are further executable to obtain, in response to detecting that the person has sanitized the one or more body parts, access credentials of the person. Additionally, the instructions are further executable to determine whether to grant access to the person based at least on the access credentials and detecting that the person has sanitized the one or more body parts.

To the accomplishment of the foregoing and related ends, the one or more aspects comprise the features hereinafter fully described and particularly pointed out in the claims. The following description and the annexed drawings set forth in detail certain illustrative features of the one or more aspects. These features are indicative, however, of but a few of the various ways in which the principles of various aspects may be employed, and this description is intended to include all such aspects and their equivalents.

DETAILED DESCRIPTION

It will be readily understood that the components of the aspects as generally described herein and illustrated in the appended figures could be arranged and designed in a wide variety of different configurations. Thus, the following more detailed description of various aspects, as represented in the figures, is not intended to limit the scope of the present disclosure, but is merely representative of various aspects. While the various aspects of the aspects are presented in drawings, the drawings are not necessarily drawn to scale unless specifically indicated.

The present solution may be embodied in other specific forms without departing from its spirit or essential characteristics. The described aspects are to be considered in all respects only as illustrative and not restrictive. The scope of the present solution is indicated by the appended claims rather than by this detailed description. All changes that come within the meaning and range of equivalency of the claims are to be embraced within their scope.

Reference throughout this specification to features, advantages, or similar language does not imply that all of the features and advantages that may be realized with the present solution should be or are in any single aspect of the present solution. Rather, language referring to the features and advantages is understood to mean that a specific feature, advantage, or characteristic described in connection with an aspect is included in at least one aspect of the present solution. Thus, discussions of the features and advantages, and similar language, throughout the specification may, but do not necessarily, refer to the same aspect.

Furthermore, the described features, advantages, and characteristics of the present solution may be combined in any suitable manner in one or more aspects. One skilled in the relevant art will recognize, in light of the description herein, that the present solution can be practiced without one or more of the specific features or advantages of a particular aspect. In other instances, additional features and advantages may be recognized in certain aspects that may not be present in all aspects of the present solution.

Reference throughout this specification to "one aspect," "an aspect," or similar language means that a particular feature, structure, or characteristic described in connection with the indicated aspect is included in at least one aspect of the present solution. Thus, the phrases "in one aspect", "in an aspect," and similar language throughout this specification may, but do not necessarily, all refer to the same aspect.

As used in this document, the singular form "a," "an," and "the" include plural references unless the context clearly dictates otherwise. Unless defined otherwise, all technical and scientific terms used herein have the same meanings as commonly understood by one of ordinary skill in the art. As used in this document, the term "comprising" means "including, but not limited to."

Conventional access control systems may facilitate the spread of a contagious disease by requiring that a person touch a surface of the access control system to provide access credentials and/or to pass through a checkpoint. That is, an infected person may touch the portion of the access control system to provide the access credentials, and subsequent persons that use the access control system may become infected as they touch the same portion of the access control system. For example, an infected person may enter a code on a keypad of the access control system, scan a keycard in a keycard scanner of the access control system, and/or provide a fingerprint scan by touching a fingerprint scanner of the access control system, and subsequent persons may be infected as they provide their access credentials to the access control system in a similar manner. Alternatively or additionally, the infected person may pull a door handle, turn a door knob, or push a turnstile to pass through the checkpoint.

Examples of the technology disclosed herein provide for multiple manners to sanitize one or more body parts (e.g., hands and/or palms) of a person and to grant access to the person that has sanitized the one or more body parts. As such, in certain aspects, the access control system may prevent a person that has not sanitized the one or more body parts from accessing a secured area controlled by the access control system. Further, aspects presented herein may reduce a risk of contagion and/or spread of a contagious disease over conventional access control systems.

These and other features of the present disclosure are discussed in detail below with regard to FIGS. 1-7.

Figure 1:
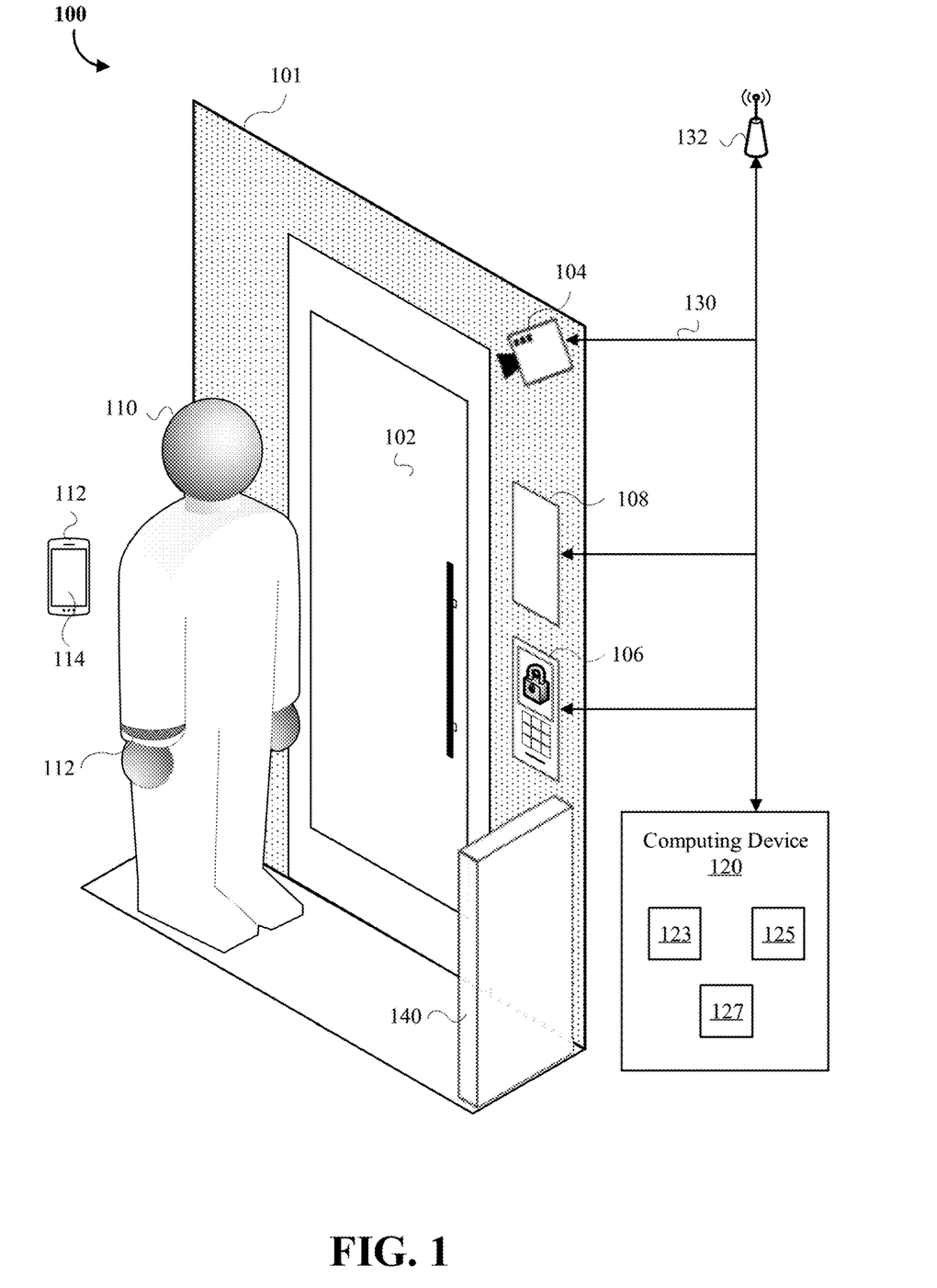
FIG. 1 is a schematic diagram illustrating an example of an access control system, in accordance with various aspects of the present disclosure.

FIG. 1 is a diagram illustrating an example of an access control system 100. The access control system 100 may be configured to grant access to a person that has sanitized one or more body parts (e.g., hands and/or palms) and has provided valid access credentials. That is, the access control system 100 may be configured to grant access to specific locations in a building and/or facility if or when the access control system 100 has detected that the person has sanitized the one or more body parts. Alternatively or additionally, the access control system 100 may be configured to restrict access to a person that has not sanitized the one or more body parts.

In some aspects, the access control system 100 may be configured to provide sanitizing features to sanitize the one or more body parts (e.g., hand sanitizer dispenser, ultraviolet ("UV") light sanitizer, hand washing station). That is, the access control system 100 may provide safety and sanitization features in addition to secure and controlled access to a secured area.

The access control area 101 may comprise a checkpoint 102. The checkpoint 102 may be a door, a gate, a turnstile, an elevator, an identification checkpoint, and/or an entryway that may prevent entry to and/or exit from a secured area. In some aspects, the checkpoint 102 may comprise a checkpoint controller mechanism. For example, the checkpoint 102 may be a locking door to a private office. The checkpoint controller mechanism of the checkpoint 102 may be actuated and/or toggled (e.g., locked, unlocked) by the access control system 100. That is, the access control system 100 may unlock the checkpoint 102 if or when the access control system 100 determines that the person 110 located at the access control area 101 is permitted to pass through the checkpoint 102. Alternatively or additionally, the access control system 100 may lock the checkpoint 102 if or when the access control system 100 determines that the person 110 located at the access control area 101 is not permitted to pass through the checkpoint 102.

The access control system 100 may employ a sensor 104 that may be arranged to capture data (e.g., visual data, infrared data, motion data) from the access control area 101. In some aspects, the access control system 100 may sense whether a person 110 is located at the access control area 101 based at least on data captured by the sensor 104. Alternatively or additionally, the access control system 100 may employ a different quantity of sensors 104 as that shown in FIG. 1, without departing from the scope described herein.

In some aspects, the sensor 104 may comprise a camera, such as a digital video camera or a security camera. The camera may capture visual data of the access control area 101 and provide the visual data to the access control system 100 to store the visual data and/or provide a live video feed to security personnel. The visual data may comprise images, video frames, and/or video feeds of the access control area 101. The camera may be generally oriented in a default direction to capture the access control area 101 where activity may be expected. Alternatively or additionally, the camera may be mounted on a gimbal that may allow for rotation and/or panning of the camera. For example, the access control system 100 may move the camera to maintain a field of view of the camera on the person 110. In some aspects, the access control system 100 may allow for manual control of the rotation and/or panning of the camera (e.g., by security personnel).

In other optional or additional aspects, the sensor 104 may comprise an infrared and/or thermal sensor. The infrared and/or thermal sensor may capture infrared and/or thermal data of the access control area 101 and provide the infrared and/or thermal data to the access control system 100. The infrared and/or thermal data may comprise heat maps, images, video frames, and/or video feeds of the access control area 101. In some aspects, the access control system 100 may determine whether the person 110 is located at the access control area 101 based on the infrared and/or thermal data.

In other optional or additional aspects, the sensor 104 may comprise a proximity and/or motion sensor. The proximity and/or motion sensor may capture motion data of the access control area 101 and provide the motion data to the access control system 100. In some aspects, the access control system 100 may determine whether the person 110 is located at the access control area 101 based on the motion data.

The access control area 101 may comprise an input device 106 configured to receive access credentials (e.g., identification card scan, biometric data) from the person 110. Alternatively or additionally, the input device 106 may provide feedback of the progress and/or status (e.g., access granted, access denied) of the identification process to the person 110. In some aspects, the input device 106 may comprise at least one scanning device, such as a magnetic stripe reader, a barcode reader, a smart chip reader, a near field communication ("NFC") reader, and a radio frequency identification ("RFID") reader. In such aspects, the access control system 100 may obtain the access credentials of the person 110 via the input device 106 by scanning a trait of the person 110 (e.g., finger-print, palm-print, iris, heart, gait) and/or an identification device presented by the person 110 (e.g., barcode, magnetic card, badge, key fob, NFC card, RFID tag, or the like.)

In other optional or additional aspects, the input device 106 may comprise a keypad, keyboard, and/or touch-sensitive display configured to receive touch input. In such aspects, the input device 106 may prompt the person 110 to enter the access credentials of the person 110 via touch input. The access credentials of the person 110 may comprise an alphanumeric passcode and/or pattern that the person 110 may enter into the input device 106 to perform the identification. For example, the input device 106 may prompt the person 110 to enter a personal identification number ("PIN") into the input device 106. In another example, the input device 106 may prompt the person 110 to enter a passcode that is shared by a group of people. That is, the shared passcode may identify the person 110 as belonging to a particular group of people (e.g., engineering department, third floor residents) associated with the shared passcode. In yet another example, the input device 106 may prompt the person 110 to enter a gesture and/or pattern into the input device 106. That is, the person 110 may be prompted to trace a shape or pattern on the touch-sensitive display of the input device 106 using one or more fingers.

In other optional or additional aspects, the input device 106 may comprise a microphone. In such aspects, the input device 106 may receive access credentials comprising voice and/or audio data from the person 110. For example, the voice and/or audio data from the person 110 may be analyzed to perform voice recognition to identify the person 110. That is, the access control system 100 may perform voice recognition analysis on a set of words or phrases spoken by the person 110 to identify the voice of the speaker as corresponding to the person 110. Alternatively or additionally, the access control system 100 may perform speech recognition analysis on a predetermined set of words or phrases (e.g., verbal passcode) spoken by the person 110 to recognize the predetermined set of words or phrases. That is, the access control system 100 may identify the person 110 based on a determination that the set of words or phrases spoken by the person 110 match a predetermined verbal passcode.

In other optional or additional aspects, the input device 106 may comprise a camera configured to receive gesture input from the person 110. In such aspects, the input device 106 may prompt the person 110 to provide the access credentials of the person 110 by performing a gesture. The camera of the input device 106 may capture body movements of the person 110 and the access control system 100 may identify the person 110 based at least on the captured body movements. For example, the access control system 100 may utilize a gesture recognition algorithm to identify the gesture performed by the person 110. Alternatively or additionally, the input device 106 may capture gesture data (e.g., body movements) from the sensor 104 (e.g., video camera, infrared camera, motion detector).

In other optional or additional aspects, the input device 106 may comprise one or more biometric sensors configured to receive biometric access credentials from the person 110. The one or more biometric sensors may comprise at least one of an iris scanner, a heartbeat scanner, and a gait sensor. In such aspects, the access control system 100 may identify the person 110 based at least on one or more of the biometric sensor data.

In other optional or additional aspects, the input device 106 may comprise a display configured to display textual, graphical, and/or video messages generated by the access control system 100. For example, the display may show alerts generated by the access control system 100 indicating that the person 110 has been granted access. For example, the display may show a green light and/or an image of an open lock to indicate that the person 110 has been granted access. Alternatively or additionally, the display may show alerts generated by the access control system 100 indicating that the person 110 has been denied access. For example, the display may show a red light and/or an image of a closed lock to indicate that the person 110 has been denied access. In some aspects, the display may show alerts generated by the access control system 100 indicating that the person 110 has not sanitized the one or more body parts.

In other optional or additional aspects, the input device 106 may comprise a speaker configured to generate an alert that may be audible by the person 110 located at the access control area 101. For example, the speaker may generate one or more sounds (e.g., a bell sound) indicating that the person 110 has been granted access. Alternatively or additionally, the speaker may generate one or more other sounds (e.g., a buzzer sound) indicating that the person 110 has been denied access. In some aspects, the speaker may comprise, or be part of, a public announcement system.

The access control system 100 may comprise a sanitizing unit 108. In some aspects, the sanitizing unit 108 may comprise an ultraviolet ("UV") light sanitizer configured to sanitize one or both palms and/or hands of the person 110 attempting to pass through the checkpoint 102. That is, the UV light sanitizer may be configured to emit UV light into a palm placement area for a UV-sanitation time duration. For example, the UV light sanitizer may emit UV-C rays which may have a wavelength such that the light energy in the UV-C rays may be converted into dissipated heat energy which may be transferred into the palm placement area and targeted on the palms and/or hands of the person 110. The power and/or wavelength of the UV-C rays may be chosen such that the UV-C rays are safe for the person 110 and cause harm to one or more microorganisms desired to be eliminated. For example, bacteria, fungus or viruses may be killed in a temperature range of 140-170 degrees Fahrenheit.

Alternatively or additionally, the UV light sanitizer may comprise one or more biometric readers (e.g., a fingerprint reader, a palm reader) configured to receive biometric access credentials from the person 110. In such aspects, the access control system 100 may identify the person 110 based at least on one or more of the biometric sensor data.

In other optional or additional aspects, the sanitizing unit 108 may comprise a sanitizing liquid (and/or gel) dispenser configured to dispense a predetermined amount of sanitizing liquid (and/or gel). That is, the person 110 may sanitize the one or more body parts (e.g., hands and/or palms) using the sanitizing liquid (and/or gel) dispensed by the access control system 100. In some aspects, the access control system 100 may detect that the person 110 sanitized the one or more body parts based at least on analysis of data (e.g., visual data, infrared data, motion data) captured by the sensor 104. For example, the access control system 100 may analyze at least one of visual data, infrared data, and motion data from the sensor 104 to determine that the person 110 applied the sanitizing liquid to the one or more body parts. In other aspects, the access control system 100 may prevent access to one or more portions of the access control system 100 (e.g., input device 106, checkpoint 102) for a predetermined time period following the dispensing of the sanitizing liquid. The predetermined time period may be configured to allow sufficient time for the person 110 to apply the sanitizing liquid to the one or more body parts. Alternatively or additionally, the access control system 100 may be configured to generate an alert indicating that a remaining amount of sanitizing liquid in a reservoir of the sanitizing unit 108 has reached a minimum threshold (e.g., 10 percent, 5 ounces, empty). The alert may comprise at least one of a audio and/or video message displayed by the input device 106 and a notification (e.g., email, short message service ("SMS"), automated voice call) transmitted to one or more recipients (e.g., security personnel, building management personnel).

In other aspects, the access control system 100 may comprise an access point ("AP") 132. The AP 132 may provide connectivity over at least one wireless communication protocol (e.g., RFID, NFC, Wireless Fidelity ("WiFi"), Light Fidelity ("LiFi"), Bluetooth, Bluetooth Low Energy ("BLE"), ZWave, Zigbee, and the like). In some aspects, the access control system 100 may detect that a user device 112 of the person 110 is within a threshold distance from the access control area 101. For example, the access control system 100 may detect that the user device 112 is within a coverage area of the AP 132.

The sensor 104, the input device 106, the AP 132, and a computing device 120 of the access control system 100 may be communicatively coupled with a network 130, such as the Internet. Other networks may also or alternatively be used, including but not limited to private intranets, corporate networks, local area networks ("LAN"), metropolitan area networks ("MAN"), wireless networks, personal networks ("PAN"), and the like. Alternatively or additionally, the sensor 104, the input device 106, the AP 132, and/or the computing device 120 may be communicatively coupled directly (e.g., hard-wired) with another element of the access control system 100 (e.g., the sensor 104, the input device 106, the AP 132, the computing device 120).

In some aspects, the user device 112 of the person 110 may communicate with the access control system 100. The user device 112 may include, but not be limited to, a laptop or tablet computer, a cellular telephone, a smart phone, a personal digital assistant ("PDA"), a handheld device, a wearable device (e.g., a smart watch, bracelet, wristband), and/or another computer device having wired and/or wireless connection capability with one or more other devices. In other aspects, the user device 112 may execute an access control application 114 for access control. For example, the user device 112 may execute the access control application 114 to communicatively couple with the access control system 100, to register an association between the user device 112 and the person 110, and/or to transmit identification information of the person 110 to the access control system 100. In other aspects, the user device 112 may communicate with the access control system 100 (e.g., input device 106, computing device 120) over a connection established via the AP 132. For example, the user device 112 may establish a connection with the access control system 100 by executing the access control application 114. For another example, the user device 112 may transmit a signal (e.g., a Bluetooth signal) to the AP 132 upon entering the range of the AP 132. The signal may indicate to the access control system 100 that the user device 112 has entered a coverage area of the AP 132. That is, the access control system 100 may determine that the user device 112 is within a threshold distance from the access control area 101.

The user device 112 may be configured to register with the access control system 100. For example, the user device 112 may provide registration information to the access control system 100 (e.g., using the access control application 114) to register an association between the person 110 and the user device 112. Alternatively or additionally, the user device 112 may register an association between the person 110 and the access control application 114. The association may indicate a correspondence between the user device 112 and the person 110. In some aspects, the access control system 100 may accept identification information of the person 110 from the user device 112 based at least on the registered association between the person 110 and the user device 112. Alternatively or additionally, the access control system 100 may reject identification information of the person 110 from another user device 112 that is not registered to the person 110.

In some aspects, the user device 112 may be configured to transmit identification information of the person 110 and/or of the user device 112 to the access control system 100 to identify the person 110. That is, the user device 112 may transmit identification information that is individually associated with the user device 112 and/or with the access control application 114. For example, the identification information may comprise an identifier generated by the person 110 (e.g., password), an identifier generated by the access control system 100 (e.g., a single-use code, a Quick Response ("QR") code), and/or an identifier of the user device 112 (e.g., a media access control ("MAC") address). The access control system 100 may identify the person 110 based at least on such identification information.

In other optional or additional aspects, the user device 112 may comprise a camera. In such aspects, the access control system 100 may obtain visual data from the camera of the user device 112. For example, the access control system 100 may determine whether the person 110 is sanitizing the one or more body parts based on the visual data from the camera of the user device 112. In other optional or additional aspects, the user device 112 may comprise one or more biometric sensors (e.g., fingerprint, heart rate, facial recognition). In such aspects, the access control system 100 may obtain biometric data from the biometric sensors of the user device 112 and identify the person 110 based at least on the biometric data.

In other optional or additional aspects, the user device 112 may comprise one or more sensors configured to detect and/or measure position, velocity, and/or acceleration changes of the one or more body parts of the person 110. For example, the user device 112 may be a wristband and/or bracelet comprising position sensors, accelerometers, vibration sensors, and the like, configured to detect and/or measure positioning and/or motion data of the hands and/or palms of the person 110. In such aspects, the access control system 100 may be configured to detect whether the person 110 has sanitized the one or more body parts based on positioning and/or motion data received from the user device 112. For example, the access control system 100 may determine, according to the positioning and/or motion data, that the person 110 has applied the sanitizing liquid. In another example, the access control system 100 may determine, according to the positioning and/or motion data, that the person 110 placed one or both palms in the palm placement area of the sanitizing unit 108.

Alternatively or additionally, the user device 112 may communicate with a sanitizing station 140 configured to detect whether the person 110 has sanitized the one or more body parts based on the positioning and/or motion data received from the user device 112. The access control system 100 may be configured to receive, from the sanitizing station 140, an indication that the person 110 has sanitized the one or more body parts of the person 110. In some aspects, the sanitizing station 140 may comprise features to sanitize the one or more body parts (e.g., a hand washing station). In such aspects, the person 110 may sanitize the one or more body parts using the sanitizing station 140 and the sanitizing station 140 may determine that the person 110 has sanitized the one or more body parts (e.g., using the position and/or motion data from user device 112). In other optional or additional aspects, the sanitizing station 140 may comprise the sanitizing unit 108.

The computing device 120 may be any type of known computer, server, or data processing device. For example, the computing device 120 may be any mobile or fixed computer device including but not limited to a computer server, a desktop or laptop or tablet computer, a cellular telephone, a PDA, a handheld device, any other computer device having wired and/or wireless connection capability with one or more other devices, or any other type of computerized device capable of processing data captured by the sensor 104 and/or input device 106. In some aspects, the computing device 120 may be a cloud-based or shared computing structure accessible through the network 130. The computing device 120 may be located in a location remote from the access control area 101, or may be integrated as part of the access control system 100.

The computing device 120 may comprise a processor 123 which may be configured to execute or implement software, hardware, and/or firmware modules that perform any functionality described herein. For example, the processor 123 may be configured to execute or implement software, hardware, and/or firmware modules that perform any functionality described herein with reference to a sanitized access control component 127 or any other component/system/device described herein.

The processor 123 may be a micro-controller, an application-specific integrated circuit ("ASIC"), a digital signal processor ("DSP"), or a field-programmable gate array ("FPGA"), and/or may comprise a single or multiple set of processors or multi-core processors. Moreover, the processor 123 may be implemented as an integrated processing system and/or a distributed processing system. The computing device 120 may further comprise a memory 125, such as for storing local versions of applications being executed by the processor 123, or related instructions, parameters, and the like.

The memory 125 may include a type of non-transitory memory usable by a computer, such as random access memory ("RAM"), read only memory ("ROM"), tapes, magnetic discs, optical discs, solid state drives ("SSDs"), volatile memory, non-volatile memory, and any combination thereof. Alternatively or additionally, the processor 123 and the memory 125 may comprise and execute an operating system executing on the processor 123, one or more applications, display drivers, etc., and/or other components of the computing device 120.

The computing device 120 may comprise a sanitized access control component 127 configured to detect whether a person 110 has sanitized one or more body parts of the person 110, to obtain access credentials of the person 110, and to determine whether to grant access to the person 110 based at least on the access credentials and detecting that the person 110 has sanitized the one or more body parts. In some aspects, the sanitized access control component 127 may be configured to sense a presence of the person 110 at an access control area 101, to dispense an amount of sanitizing liquid, to capture the access credentials of the person 110, to instruct a checkpoint controller of the access control system 100 to remain in a locked state, and to emit UV light into a palm placement area.

Aspects of the present disclosure may be implemented using hardware, software, or a combination thereof and may be implemented in one or more computer systems or other processing systems. In an aspect of the present disclosure, features are directed toward one or more computer systems capable of carrying out the functionality described herein. An example of such a computer system is shown in FIG. 2.

Figure 2:
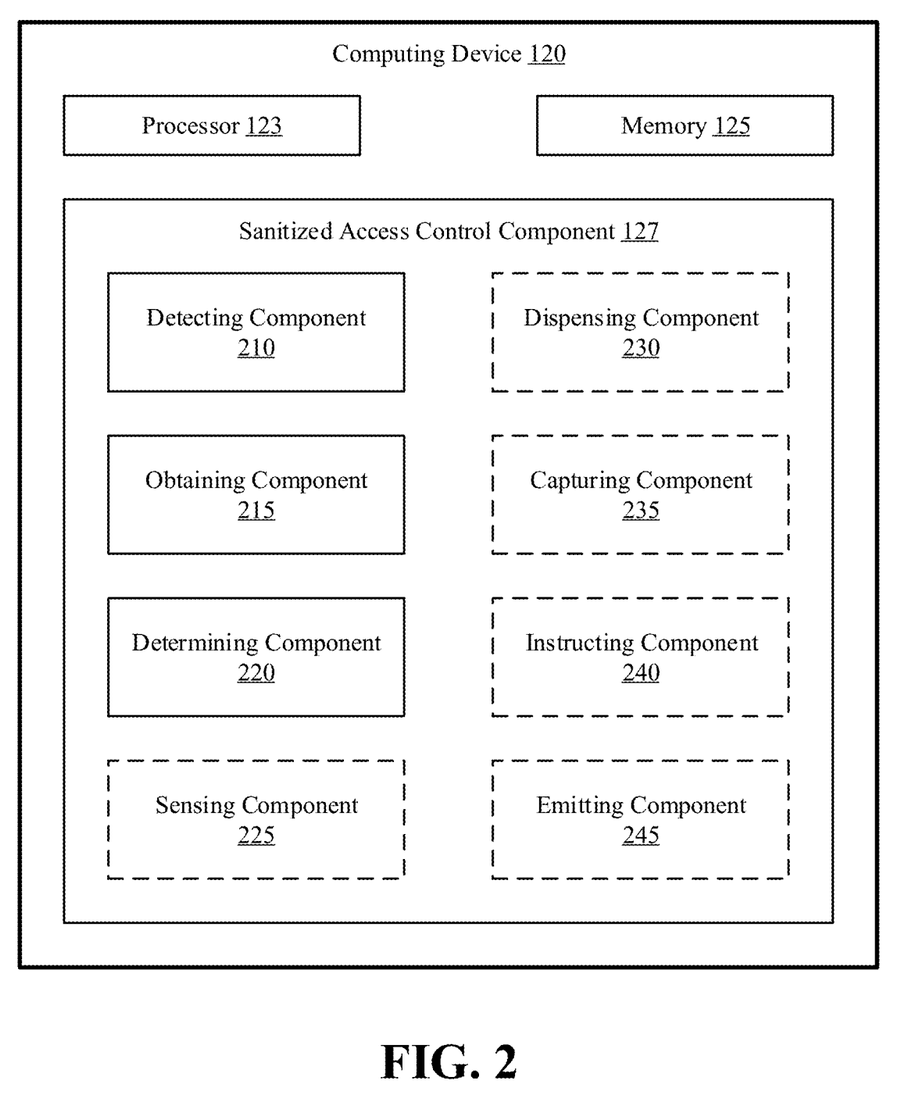
FIG. 2 is a block diagram of an example apparatus such as a computing device for operating an access control system, in accordance with various aspects of the present disclosure.

FIG. 2 is a block diagram of an example computing device 120 for operating the access control system 100. The computing device 120 depicted in FIG. 2 is similar in many respects to the computing device 120 described above with reference to FIG. 1, and may include additional features not mentioned above. In some aspects, the computing device 120 may comprise a processor 123 configured to execute or implement software, hardware, and/or firmware modules that perform any functionality described herein (e.g., sanitized access control component 127), a memory 125 configured to store computer-executable instructions for execution by the processor 123, and a sanitized access control component 127 configured to sanitize one or more body parts of a person 110 and to grant access to the person 110 that has sanitized the one or more body parts.

In some aspects, the computing device 120 may be configured to perform one or more operations described herein in connection with FIG. 1. Alternatively or additionally, the computing device 120 may be configured to perform one or more processes described herein, such as method 300 of FIGS. 3-7. In other aspects, the computing device 120 may include one or more components of the computing device 120 described above in connection with FIG. 1.

In some aspects, the sanitized access control component 127 may include a set of components, such as a detecting component 210 configured to detect whether the person 110 has sanitized one or more body parts of the person 110, an obtaining component 215 configured to obtain access credentials of the person 110, and a determining component 220 configured to determine whether to grant access to the person 110. Optionally, the sanitized access control component 127 may further include a sensing component 225 configured to sense a presence of the person 110 at the access control area 101, a dispensing component 230 configured to dispense an amount of sanitizing liquid, a capturing component 235 configured to capture the access credentials of the person 110, an instructing component 240 configured to instruct a checkpoint controller of the access control system 100, and an emitting component 245 configured to emit UV light into a palm placement area.

Alternatively or additionally, the set of components may be separate and distinct from the sanitized access control component 127. In other aspects, one or more components of the set of components may include or may be implemented within a controller/processor (e.g., processor 123), a memory (e.g., memory 125), or a combination thereof, of the computing device 120 described in FIGS. 1-2. Alternatively or additionally, one or more components of the set of components may be implemented at least in part as software stored in a memory, such as the memory 125. For example, a component (or a portion of a component) may be implemented as computer-executable instructions or code stored in a non-transitory computer-readable medium and executable by a controller or a processor to perform the functions or operations of the component.

The number and arrangement of components shown in FIG. 2 are provided as an example. In practice, there may be additional components, fewer components, different components, or differently arranged components than those shown in FIG. 2. Furthermore, two or more components shown in FIG. 2 may be implemented within a single component, or a single component shown in FIG. 2 may be implemented as multiple, distributed components. Additionally or alternatively, a set of (one or more) components shown in FIG. 2 may perform one or more functions described as being performed by another set of components shown in FIG. 1.

Referring to FIGS. 3-7, in operation, the computing device 120 may perform a method 300 of operating the access control system 100. The method 300 may be performed by the computing device 120 (which may include the memory 125 and which may be the entire computing device 120 and/or one or more components of the computing device 120, such as the sanitized access control component 127, the processor 123, and/or the memory 125.) The method 300 may be performed by the sanitized access control component 127 in communication with the sensor 104, the input device 106, and the sanitizing unit 108.

Figure 3:
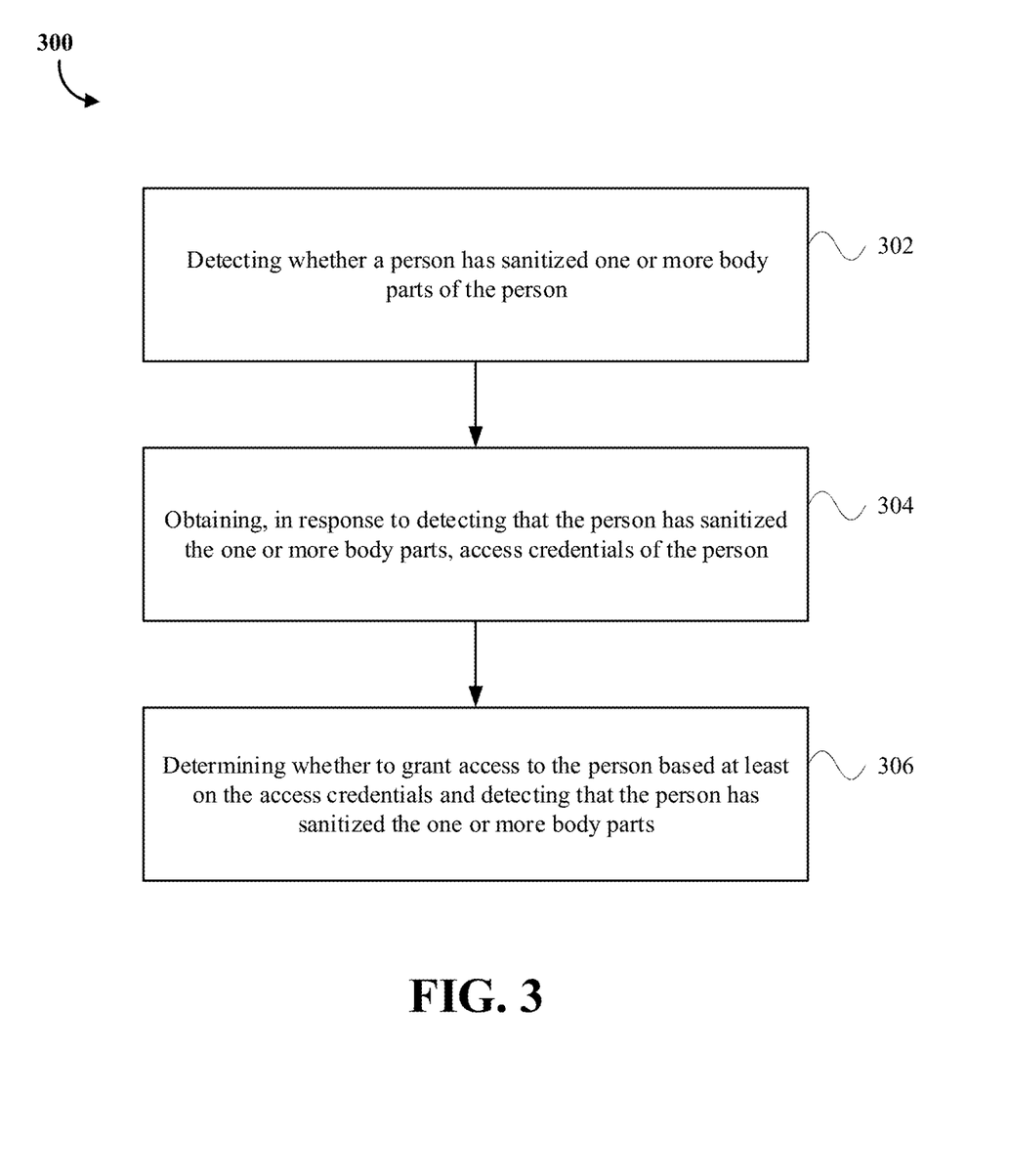
FIG. 3 is a flowchart of a method of operating an access control system to be performed by a computing device, in accordance with various aspects of the present disclosure.

At block 302, the method 300 includes detecting whether a person has sanitized one or more body parts of the person. For example, in an aspect, the computing device 120, the processor 123, the memory 125, the sanitized access control component 127, and/or the detecting component 210 may be configured to or may comprise means for detecting whether the person 110 has sanitized the one or more body parts of the person 110.

For example, the detecting at block 302 may include receiving data (e.g., visual data, infrared data, motion data) of the access control area 101 from the sensor 104. The visual data may comprise images, video frames, and/or video feeds of the access control area 101. The infrared and/or thermal data may comprise heat maps, images, video frames, and/or video feeds of the access control area 101.

In some aspects, the detecting at block 302 may include classifying objects that appear in the received data and determining whether objects that appear in the received data constitute a person 110. That is, the detecting at block 302 may implement one or more classification techniques for classifying an object that appears in the received data as a person 110. The one or more classification techniques may include accessing a database or other data store of images and using image processing algorithms, machine learning classifiers, and the like on the received data to establish which object appearing in the received data may likely represent the person 110. Alternatively or additionally, the one or more classification techniques may include accessing base images of the access control area 101 in which no persons appear and comparing the base images with the received data to detect additional objects in the received data and determine whether the additional objects may represent the person 110. In other aspects, the one or more classification techniques may include placing bounding boxes around objects identified in the received data, and discarding bounding boxes whose dimensions do not meet certain thresholds (e.g., height, width, footprint) as likely non-human objects.

In other optional or additional aspects, the detecting at block 302 may include extracting visual characteristics of the person 110 classified from the received data. The visual characteristics may be extracted using a visual characteristics detection algorithm that may be configured to detect visual characteristics of the person 110 from the received data. For example, the visual characteristics detection algorithm may comprise a machine learning classifier having been trained to extract visual characteristics (e.g., hands, arms, legs, torso, head, face) from visual data in which the person 110 appears. Alternatively or additionally, the visual characteristics detection algorithm may compare properties of base images of visual characteristics with the properties of the visual data, such as color (e.g., hue, lightness, or saturation), object shape (e.g., shape of face), object size (e.g., of person), and/or other conventional image comparison attributes.

In other optional or additional aspects, the detecting at block 302 may include detecting that the person 110 has sanitized the one or more body parts (e.g., hands and/or palms) based at least on the extracted visual characteristics of the person 110. For example, the visual characteristics may indicate that the person 110 moved one or both hands and/or arms in a manner indicative of a sanitizing motion. That is, the visual characteristics may indicate that the person 110 has applied the sanitizing liquid. In another example, the visual characteristics may indicate that the person 110 placed one or both palms in the palm placement area of the sanitizing unit 108.

In other optional or additional aspects, the detecting at block 302 may include receiving, from the user device 112, position, velocity, and/or acceleration changes of the one or more body parts of the person 110. For example, the user device 112 may be a wristband and/or bracelet comprising position sensors, accelerometers, vibration sensors, and the like, configured to detect and/or measure positioning and/or motion data of the hands and/or palms of the person 110. In such aspects, the detecting at block 302 may include detecting whether the person 110 has sanitized the one or more body parts based on the positioning and/or motion data received from the user device 112. For example, the detecting at block 302 may include determining, according to the positioning and/or motion data, that the person 110 has applied the sanitizing liquid. In another example, the detecting at block 302 may include determining, according to the positioning and/or motion data, that the person 110 placed one or both palms in the palm placement area of the sanitizing unit 108.

In other optional or additional aspects, the detecting at block 302 may include measuring a time duration that the person 110 sanitized the one or more body parts. For example, the detecting at block 302 may include measuring how long the person 110 applied the sanitizing liquid to the one or more body parts. In another example, the detecting at block 302 may include measuring how long the person 110 placed one or both palms in the palm placement area of the sanitizing unit 108. In such aspects, the detecting at block 302 may include detecting that the person 110 sanitized the one or more body parts if or when the measured time duration exceeds a minimum time threshold. In some aspects, the minimum time threshold may be configured according to the steps used to sanitize the one or more body parts. For example, the minimum time threshold may be configured to a first value if or when the person 110 sanitized the one or more body parts using the sanitizing liquid. In another example, the minimum time threshold may be configured to a second value if or when the person 110 sanitized the one or more body parts using the UV light sanitizer. Alternatively or additionally, the minimum time threshold may be configured according to the quantity and/or type of body part that is sanitized. For example, the minimum time threshold may be configured to a first value if or when the person 110 sanitized one hand and/or palm. In another example, the minimum time threshold may be configured to a second value if or when the person 110 sanitized both hands and/or palms.

In other optional or additional aspects, the detecting at block 302 may include detecting that the sanitizing unit 108 has been activated. For example, the detecting at block 302 may include detecting that the person 110 has sanitized the one or more body parts based on the sanitizing liquid (and/or gel) dispenser having dispensed the predetermined amount of sanitizing liquid. Alternatively or additionally, the detecting at block 302 may include detecting that the person 110 has sanitized the one or more body parts based on the UV light sanitizer of the sanitizing unit 108 having emitted UV light.

Further, for example, the detecting at block 302 may be performed to allow the access control system 100 to prevent a person 110 that has not sanitized their hands and/or palms (e.g., one or more body parts) from accessing a secured area controlled by the access control system 100. Thus, aspects presented herein may reduce a risk of contagion and/or spread of a contagious disease over conventional access control systems.

In an optional aspect, the detecting at block 302 may comprise receiving, from a sanitizing station 140, an indication that the person 110 has sanitized the one or more body parts of the person 110.

For example, the detecting at block 302 may include the user device 112 communicating with the sanitizing station 140. The sanitizing station 140 having been configured to detect whether the person 110 has sanitized the one or more body parts based on the positioning and/or motion data received from the user device 112. In some aspects, the person 110 may sanitize the one or more body parts using the sanitizing station 140 and the sanitizing station 140 may determine that the person 110 has sanitized the one or more body parts (e.g., using the position and/or motion data from user device 112). Further, for example, the detecting at block 302 may be performed to provide sanitizing features to sanitize the one or more body parts of the person 110. Thus, aspects presented herein may provide safety and sanitization features in addition to secure and controlled access to a secured area.

At block 304, the method 300 includes obtaining, in response to detecting that the person has sanitized the one or more body parts, access credentials of the person. For example, in an aspect, the computing device 120, the processor 123, the memory 125, the sanitized access control component 127, and/or the obtaining component 215 may be configured to or may comprise means for obtaining, in response to detecting that the person 110 has sanitized the one or more body parts, the access credentials of the person 110.

For example, the obtaining at block 304 may include obtaining voice and/or audio data of the person 110. The voice and/or audio data may comprise a set of words and/or phrases spoken by the person 110 for identification purposes. For example, the obtaining at block 304 may include obtaining the voice and/or audio data from a microphone of the input device 106. Alternatively or additionally, the obtaining at block 304 may include obtaining other voice and/or audio data from a microphone of the user device 112 that is registered to the person 110.

In some aspects, the obtaining at block 304 may include obtaining gesture data of the person 110. The gesture data may comprise body movements of the person 110 while performing a gesture. For example, the obtaining at block 304 may include obtaining the gesture data from the camera of the input device 106 and/or from the camera of the sensor 104. Alternatively or additionally, the obtaining at block 304 may include obtaining other gesture data from the camera of the user device 112 that is registered to the person 110.

In other optional or additional aspects, the obtaining at block 304 may include obtaining identification information of the person 110 from a card scanner, a NFC reader, and/or a RFID reader of the input device 106. In such aspects, the obtaining at block 304 may include performing a scan of an identification device presented by the person 110 (e.g., badge, key fob, NFC card, RFID tag, or the like) to read the identification information. Alternatively or additionally, the obtaining at block 304 may include obtaining identification information from an identification device comprised by the user device 112 that is registered to the person 110.

In other optional or additional aspects, the obtaining at block 304 may include obtaining iris scan data of the person 110. The iris scan data may comprise biometric data corresponding to one or both irises of the person 110. For example, the obtaining at block 304 may include obtaining the iris scan data from an iris scanner of the input device 106 and/or from the camera of the sensor 104. Alternatively or additionally, the obtaining at block 304 may include obtaining other iris scan data from the camera of the user device 112 that is registered to the person 110.

In other optional or additional aspects, the obtaining at block 304 may include obtaining heartbeat scan data of the person 110. The heartbeat scan data may comprise biometric data corresponding to a geometry (e.g., size, shape) of a heart of the person 110 and/or to a beating pattern of the heart. For example, obtaining at block 304 may include obtaining the heartbeat scan data from a heartbeat scanner of the input device 106. Alternatively or additionally, the obtaining at block 304 may include obtaining other heartbeat scan data from a heartbeat scanner of the user device 112 that is registered to the person 110.

In other optional or additional aspects, the obtaining at block 304 may include obtaining gait scan data of the person 110. The gait scan data may comprise biometric data corresponding to a walking style and/or pace of the person 110. For example, the obtaining at block 304 may include obtaining the gait scan data from a gait sensor of the input device 106 and/or from the camera of the sensor 104. Alternatively or additionally, the obtaining at block 304 may include obtaining other gait scan data from the camera of the user device 112 that is registered to the person 110.

In other optional or additional aspects, the obtaining at block 304 may include obtaining registration information of the user device 112 of the person 110. That is, the obtaining at block 304 may include registering an association between the person 110 and the user device 112 of the person 110. Alternatively or additionally, the obtaining at block 304 may include registering an association between the person 110 and the access control application 114 executed by the user device 112. The association may indicate a correspondence between the user device 112 and the person 110. In some aspects, the obtaining at block 304 may include accepting identification information of the person 110 from the user device 112 based at least on the registered association between the person 110 and the user device 112. Alternatively or additionally, the obtaining at block 304 may include rejecting identification information of the person 110 from another user device 112 that is not registered to the person 110.

In other optional or additional aspects, the obtaining at block 304 may include obtaining identification information from the user device 112 of the person 110. The identification information may be individually associated with the user device 112 and/or with the access control application 114. For example, the identification information may comprise an identifier generated by the person 110 (e.g., password), an identifier generated by the access control system 100 (e.g., a single-use code, a QR code), and/or an identifier of the user device 112 (e.g., a MAC address). In some aspects, the obtaining at block 304 may include obtaining the identification information by receiving the identification information that has been transmitted by the user device 112. In other optional or additional aspects, the obtaining at block 304 may include obtaining the identification information that is displayed by the user device 112 using the camera of the sensor 104 and/or the camera of the input device 106. For example, the user device 112 and/or the access control application 114 may display an image-based code (e.g., a QR code) and the obtaining at block 304 may include obtaining receive visual data comprising the image-based code from the camera of the sensor 104 and/or the camera of the input device 106.

In other optional or additional aspects, the obtaining at block 304 may include preventing the obtaining of the access credentials if or when the detecting at block 302 detected that the person 110 has not sanitized the one or more body parts. Alternatively or additionally, the obtaining at block 304 may include disabling the input device 106 if or when the detecting at block 302 detected that the person 110 has not sanitized the one or more body parts. That is, the obtaining at block 304 may include preventing the person 110 from providing access credentials if or when the detecting at block 302 detected that the person 110 has not sanitized the one or more body parts.

Further, for example, the obtaining at block 304 may be performed to obtain access credentials of the person 110 with which the person 110 may be identified. The access credentials may allow the access control system 100 to determine whether the person 110 is to be granted/denied access to an specific location in a building and/or facility.

In optional or additional aspects, the obtaining at block 304 may comprise capturing, via a scanning device of the access control system 100, the access credentials of the person 110. In such aspects, the scanning device may be configured to capture at least one of an access code, a fingerprint, a palm print, a facial image, a vocal input, an iris scan, a heartbeat scan, an identity card barcode, a QR code, and identification information from a device of the person 110.

For example, the obtaining at block 304 may include capturing, by a scanning device of the input device 106, access credentials of the person 110. In some aspects, the obtaining component may be configured to obtain the captured credentials from the input device 106.

At block 306, the method 300 includes determining whether to grant access to the person based at least on the access credentials and detecting that the person has sanitized the one or more body parts. For example, in an aspect, the computing device 120, the processor 123, the memory 125, the sanitized access control component 127, and/or the determining component 220 may be configured to or may comprise means for determining whether to grant the access to the person 110 based at least on the access credentials and detecting that the person 110 has sanitized the one or more body parts.

For example, the determining at block 306 may include identifying the person 110 based at least on the access credentials obtained at block 304. In some aspects, the determining at block 306 may include performing voice recognition analysis on the voice and/or audio data of the person 110. That is, the determining at block 306 may include performing voice recognition analysis on a set of words or phrases spoken by the person 110 to identify the voice of the speaker as corresponding to the person 110. For example, the determining at block 306 may include comparing the voice and/or audio data with previously recorded voice and/or audio data that is known to have been spoken by the person 110. Alternatively or additionally, the determining at block 306 may include performing speech recognition analysis on a predetermined set of words or phrases (e.g., verbal passcode) spoken by the person 110 to recognize the predetermined set of words or phrases. That is, the determining at block 306 may include identifying the person 110 based on a determination that the set of words or phrases spoken by the person 110 match a predetermined verbal passcode corresponding to the person 110.

In other optional or additional aspects, the determining at block 306 may include identifying the person 110 based at least on gesture data of the person 110. In such aspects, the determining at block 306 may include interpreting the body movements of the person 110 while performing a gesture.

The determining at block 306 may include identifying the person 110 based at least on a determination that the gesture performed by the person 110 matches a predetermined gesture corresponding to the person 110.

In other optional or additional aspects, the determining at block 306 may include identifying the person 110 based at least on access credentials obtained from a scan of an identification device presented by the person 110 (e.g., badge, key fob, NFC card, RFID tag, wearable device, or the like). That is, the determining at block 306 may include identifying the person 110 based at least on a determination that the access credentials obtained from the scan corresponds to the person 110.

In other optional or additional aspects, the determining at block 306 may include identifying the person 110 based at least on iris scan data of the person 110. That is, the determining at block 306 may include identifying the person 110 based at least on a determination that the iris scan data corresponds to the person 110.

In other optional or additional aspects, the determining at block 306 may include identifying the person 110 based at least on heartbeat scan data of the person 110. That is, the determining at block 306 may include identifying the person 110 based at least on a determination that the heartbeat scan data corresponds to the person 110.

In other optional or additional aspects, the determining at block 306 may include identifying the person 110 based at least on gait scan data of the person 110. That is, the determining at block 306 may include identifying the person 110 based at least on a determination that the gait scan data corresponds to the person 110.

In other optional or additional aspects, the determining at block 306 may include identifying the person 110 based at least on identification information of the person 110 received from the user device 112. That is, the determining at block 306 may include identifying the person 110 based at least on a determination that the identification information of the person 110 received from the user device 112 corresponds to the person 110. For example, the determining at block 306 may include identifying the person 110 based at least on a determination that a QR code displayed by the user device 112 corresponds to the person 110.

In other optional or additional aspects, the determining at block 306 may include determining whether the person 110 should be granted entry/exit based at least on a determination that the access credentials identifies the person 110 and that the person 110 has sanitized the one or more body parts. That is, the determining at block 306 may include determining whether the person 110 is permitted to be granted entry/exit if or when the person 110 has sanitized the one or more body parts. In some aspects, the determining at block 306 may include granting access to the person 110 if or when the determining at block 306 has determined that the person 110 should be granted entry and that the person 110 has sanitized the one or more body parts. For example, if or when the determining at block 306 has determined to grant access (e.g., entry, exit) to the person 110, the determining at block 306 may include unlocking the checkpoint controller mechanism of the checkpoint 102, showing on the display of the input device 106 a green light and/or an image of an open lock, and/or generating, with the speaker of the input device 106, one or more sounds (e.g., a bell sound) indicating that the person 110 has been granted access.

In other optional or additional aspects, the determining at block 306 may include causing the access control system 100 to deny access to the person 110 if or when the determining at block 306 has determined that the person 110 should not be granted access or determined that the person 110 has not sanitized the one or more parts. For example, if or when the determining at block 306 has determined to deny access to the person 110, the determining at block 306 may include locking the checkpoint controller mechanism of the checkpoint 102, showing on the display of the input device 106 a red light and/or an image of a closed lock, and/or generating, with the speaker of the input device 106, one or more sounds (e.g., a buzzer sound) indicating that the person 110 has been denied access.

Further, for example, the determining at block 306 may be performed to identify the person 110 and determine whether the person 110 that has sanitized the one or more body parts is to be granted/denied access to an specific location in a building and/or facility. As such, in certain aspects, the access control system 100 may prevent a person 110 that has not sanitized the one or more body parts from accessing a secured area controlled by the access control system 100. Thus, aspects presented herein may reduce a risk of contagion and/or spread of a contagious disease over conventional access control systems.

Figure 4:
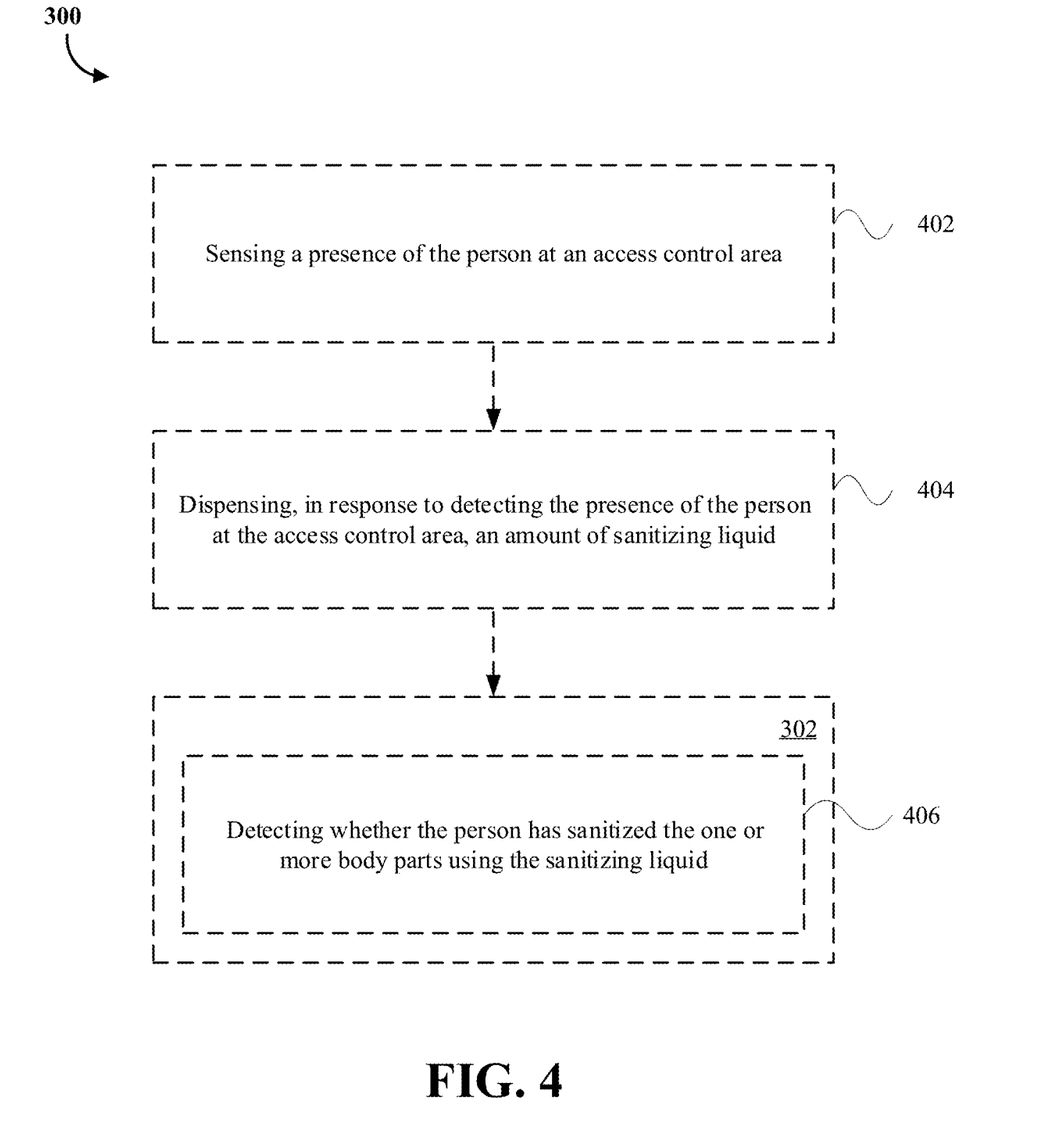
FIG. 4 is a flowchart of first additional or optional steps of the method of operating an access control system to be performed by the computing device, in accordance with various aspects of the present disclosure.

Referring to FIG. 4, in an optional or additional aspect that may be combined with any other aspect, at block 402, the method 300 may further include sensing a presence of the person at an access control area. For example, in an aspect, the computing device 120, the processor 123, the memory 125, the sanitized access control component 127, and/or the sensing component 225 may be configured to or may comprise means for sensing the presence of the person 110 at the access control area 101.

For example, the sensing at block 402 may include detecting the presence of the person 110 based on data (e.g., visual data, infrared data, motion data) received from the sensor 104. That is, the sensing at block 402 may include determining that an objects appearing in the received data constitutes the person 110.

In some aspects, the sensing at block 402 may include detecting that the user device 112 of the person 110 is within a threshold distance of the access control area 101. For example, the sensing at block 402 may include detecting that the user device 112 is within a coverage area of the AP 132.

Further, for example, the sensing at block 402 may be performed to provide an indication to the access control system 100 that the person 110 is requesting access to the secure area controlled by the access control system 100. As such, the access control system 100 may automatically dispense an amount of sanitizing liquid as the person 110 approaches the access control area 101.

In this optional or additional aspect, at block 404, the method 300 may include dispensing, in response to detecting the presence of the person at the access control area 101, an amount of sanitizing liquid. For example, in an aspect, the computing device 120, the processor 123, the memory 125, the sanitized access control component 127, and/or the dispensing component 230 may be configured to or may comprise means for dispensing, in response to detecting the presence of the person 110 at the access control area 101, the amount of sanitizing liquid.

For example, the dispensing at block 404 may include commanding the sanitizing liquid (and/or gel) dispenser of the sanitizing unit 108 to dispense the predetermined amount of sanitizing liquid. That is, the dispensing at block 404 may include actuating a pump and/or motor of the sanitizing liquid (and/or gel) dispenser of the sanitizing unit 108 to cause the dispenser to dispense the predetermined amount of sanitizing liquid. The predetermined amount of sanitizing liquid may be sufficient for the person 110 to sanitize the one or more body parts (e.g., hands and/or palms).

Further, for example, the dispensing at block 404 may be performed to provide sanitizing features for the person 110 to sanitize the one or more body parts. Thus, aspects presented herein may provide safety and sanitization features in addition to secure and controlled access to a secured area.

In this optional or additional aspect, at block 406, the detecting at block 302 of detecting whether the person 110 has sanitized the one or more body parts of the person 110 may include detecting whether the person has sanitized the one or more body parts using the sanitizing liquid. For example, in an aspect, the computing device 120, the processor 123, the memory 125, the sanitized access control component 127, and/or the detecting component 210 may be configured to or may comprise means for detecting whether the person 110 has sanitized the one or more body parts using the sanitizing liquid.

For example, the detecting at block 406 may include determining whether the person 110 moved one or both hands and/or arms in a manner indicative of applying the sanitizing liquid. That is, the detecting at block 406 may include determining whether the visual characteristics extracted from visual data received from sensor 104 indicate that the person 110 has applied the sanitizing liquid.

In some aspects, the detecting at block 406 may include detecting whether the person 110 has applied the sanitizing liquid to the one or more body parts based on position and/or motion data received from the user device 112.

Further, for example, the detecting at block 406 may be performed allow the access control system 100 to prevent a person 110 that has not sanitized their hands and/or palms (e.g., one or more body parts) from accessing a secured area controlled by the access control system 100. Thus, aspects presented herein may reduce a risk of contagion and/or spread of a contagious disease over conventional access control systems.

Figure 5:
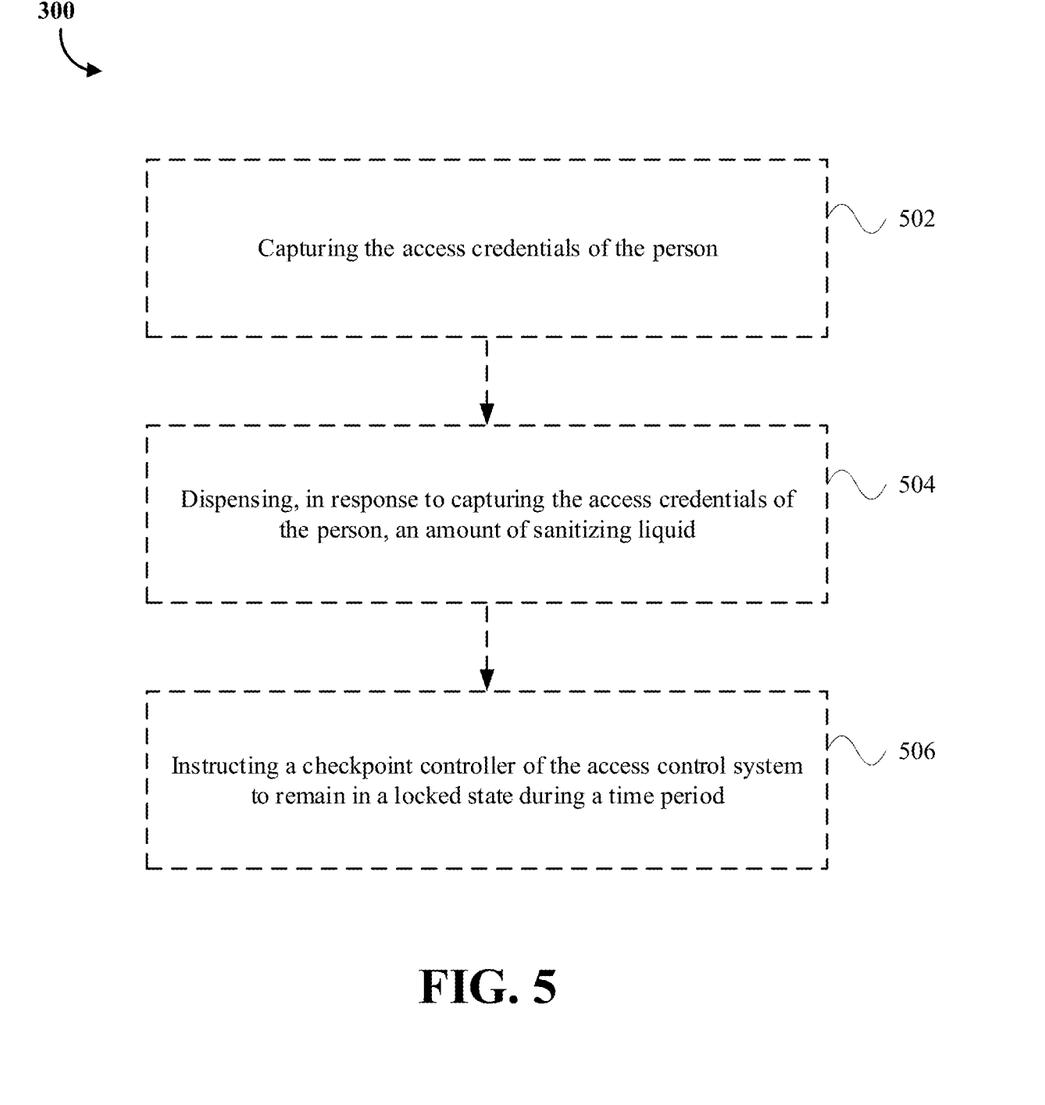
FIG. 5 is a flowchart of second additional or optional steps of the method of operating an access control system to be performed by the computing device, in accordance with various aspects of the present disclosure.

Referring to FIG. 5, in an optional or additional aspect that may be combined with any other aspect, at block 502, the method 300 may further include capturing the access credentials of the person. For example, in an aspect, the computing device 120, the processor 123, the memory 125, the sanitized access control component 127, and/or the capturing component 235 may be configured to or may comprise means for capturing the access credentials of the person.

For example, the capturing at block 502 may include capturing, by the scanning device of the input device 106, the access credentials of the person 110. In some aspects, the obtaining component may be configured to obtain the captured credentials from the input device 106. In some aspects, the scanning device may be configured to capture at least one of an access code, a fingerprint, a palm print, a facial image, a vocal input, an iris scan, a heartbeat scan, an identity card barcode, a QR code, and identification information from a device of the person 110.

Further, for example, the capturing at block 502 may be performed to provide an indication to the access control system 100 that the person 110 is requesting access to the secure area controlled by the access control system 100. As such, the access control system 100 may automatically dispense an amount of sanitizing liquid to the person 110 as the person 110 presents access credentials.

In this optional or additional aspect, at block 504, the method 300 may include dispensing, in response to capturing the access credentials of the person, an amount of sanitizing liquid. For example, in an aspect, the computing device 120, the processor 123, the memory 125, the sanitized access control component 127, and/or the dispensing component 230 may be configured to or may comprise means for dispensing, in response to capturing the access credentials of the person 110, an amount of sanitizing liquid.

For example, the dispensing at block 504 may include commanding the sanitizing liquid (and/or gel) dispenser of the sanitizing unit 108 to dispense the predetermined amount of sanitizing liquid. That is, the dispensing at block 504 may include actuating a pump and/or motor of the sanitizing liquid (and/or gel) dispenser of the sanitizing unit 108 to cause the dispenser to dispense the predetermined amount of sanitizing liquid. The predetermined amount of sanitizing liquid may be sufficient for the person 110 to sanitize the one or more body parts (e.g., hands and/or palms).

Further, for example, the dispensing at block 504 may be performed to provide sanitizing features for the person 110 to sanitize the one or more body parts. Thus, aspects presented herein may provide safety and sanitization features in addition to secure and controlled access to a secured area.

In this optional or additional aspect, at block 506, the method 300 may include instructing a checkpoint controller of the access control system to remain in a locked state during a time period, the time period being configured according to a time duration needed to apply the sanitizing liquid. For example, in an aspect, the computing device 120, the processor 123, the memory 125, the sanitized access control component 127, and/or the instructing component 240 may be configured to or may comprise means for instructing a checkpoint controller of the access control system 100 to remain in a locked state during a time period, the time period being configured according to a time duration needed to apply the sanitizing liquid.

For example, the instructing at block 506 may include actuating and/or toggling the checkpoint controller mechanism of the checkpoint 102 into a locked position. In some aspects, the instructing at block 506 may include preventing changes to the locking state of the checkpoint controller mechanism until the time period has expired. For example, the person 110 may not be permitted to gain access through the checkpoint 102 until the time period has expired.

Further, for example, the instructing at block 506 may be performed to provide the person 110 with sufficient time to sanitize the one or more body parts using the sanitizing liquid. As such, the access control system 100 may provide sanitizing features for the person 110 to sanitize the one or more body parts. Further, the access control system 100 may prevent a person 110 that has not sanitized the one or more body parts from accessing a secured area controlled by the access control system 100. Thus, aspects presented herein may provide safety and sanitization features in addition to secure and controlled access to a secured area.

Figure 6:
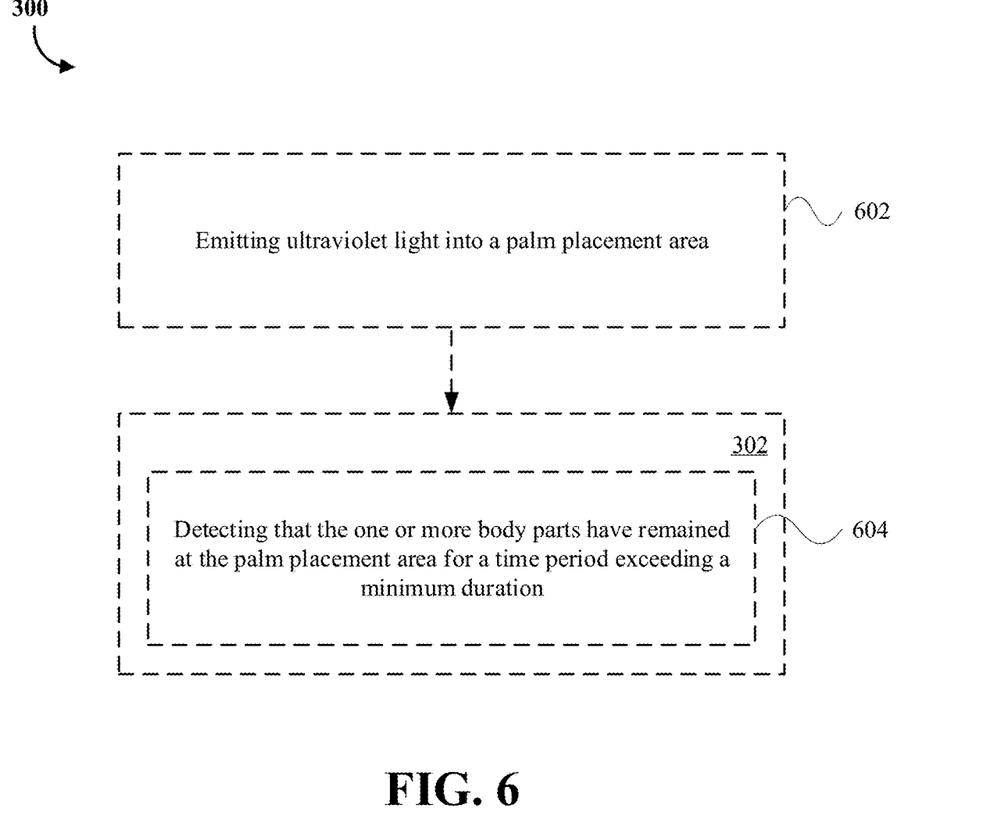
FIG. 6 is a flowchart of third additional or optional steps of the method of operating an access control system to be performed by the computing device, in accordance with various aspects of the present disclosure.

Referring to FIG. 6, in an optional or additional aspect that may be combined with any other aspect, at block 602, the method 300 may further include emitting ultraviolet light into a palm placement area. For example, in an aspect, the computing device 120, the processor 123, the memory 125, the sanitized access control component 127, and/or the emitting component 245 may be configured to or may comprise means for emitting the ultraviolet light into the palm placement area.

For example, the emitting at block 602 may include emitting UV light into the palm placement area for a UV-sanitation time duration. For example, the emitting at block 602 may include emitting UV-C rays which may have a wavelength such that the light energy in the UV-C rays may be converted into dissipated heat energy which may be transferred into the palm placement area and targeted on the palms and/or hands of the person 110. The power and/or wavelength of the UV-C rays may be chosen such that the UV-C rays are safe for the person 110 and lethal to one or more microorganisms desired to be eliminated. For example, bacteria, fungus or viruses may be killed in a temperature range of 140-170 degrees Fahrenheit.

Further, for example, the emitting at block 602 may be performed provide sanitizing features for the person 110 to sanitize the one or more body parts. Thus, aspects presented herein may provide safety and sanitization features in addition to secure and controlled access to a secured area.

In this optional or additional aspect, at block 604, the detecting at block 302 of detecting whether the person 110 has sanitized the one or more body parts of the person 110 may include detecting that the one or more body parts have remained at the palm placement area during a time period exceeding a minimum duration. For example, in an aspect, the computing device 120, the processor 123, the memory 125, the sanitized access control component 127, and/or the detecting component 210 may be configured to or may comprise means for detecting that the one or more body parts have remained at the palm placement area during a time period exceeding a minimum duration.

For example, the detecting at block 604 may include measuring how long the person 110 placed one or both palms in the palm placement area of the sanitizing unit 108. That is, the detecting at block 604 may include detecting that the person 110 sanitized the one or more body parts if or when the measured time duration exceeds the minimum time threshold.

Further, for example, the detecting at block 604 may be performed to allow the access control system 100 to prevent a person 110 that has not sanitized their hands and/or palms (e.g., one or more body parts) from accessing a secured area controlled by the access control system 100. Thus, aspects presented herein may reduce a risk of contagion and/or spread of a contagious disease over conventional access control systems.

Figure 7:
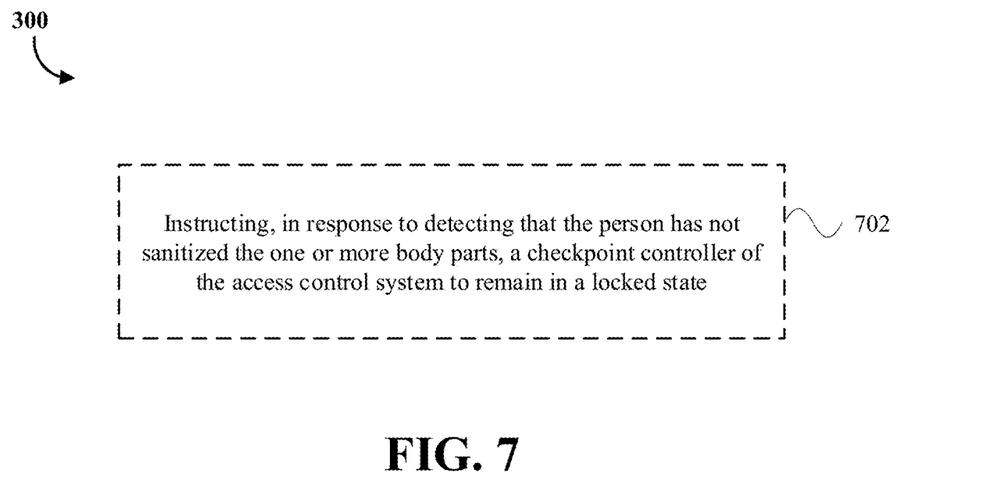
FIG. 7 is a flowchart of fourth additional or optional steps of the method of operating an access control system to be performed by the computing device, in accordance with various aspects of the present disclosure.

Referring to FIG. 7, in an optional or additional aspect that may be combined with any other aspect, at block 702, the method 300 may further include instructing, in response to detecting that the person has not sanitized the one or more body parts, a checkpoint controller of the access control system to remain in a locked state. For example, in an aspect, the computing device 120, the processor 123, the memory 125, the sanitized access control component 127, and/or the instructing component 240 may be configured to or may comprise means for instructing, in response to detecting that the person 110 has not sanitized the one or more body parts, a checkpoint controller of the access control system 100 to remain in a locked state.

For example, the instructing at block 702 may include actuating and/or toggling the checkpoint controller mechanism of the checkpoint 102 into a locked position. In some aspects, the instructing at block 702 may include preventing changes to the locking state of the checkpoint controller mechanism until the person 110 has sanitized the one or more parts. For example, the person 110 may not be permitted to gain access through the checkpoint 102 until the person 110 has sanitized the one or more parts.

Further, for example, the instructing at block 702 may be performed prevent a person 110 that has not sanitized the one or more body parts from accessing a secured area controlled by the access control system 100. Thus, aspects presented herein may provide safety and sanitization features in addition to secure and controlled access to a secured area.

It is understood that the specific order or hierarchy of blocks in the processes/flowcharts disclosed is an illustration of example approaches. Based upon design preferences, it is understood that the specific order or hierarchy of blocks in the processes/flowcharts may be rearranged. Further, some blocks may be combined or omitted. The accompanying method claims present elements of the various blocks in a sample order, and are not meant to be limited to the specific order or hierarchy presented.

In one or more aspects, the functions described herein may be implemented in hardware, software, firmware, or any combination thereof. If or when implemented in software, the functions may be stored or transmitted as one or more instructions or code on a computer-readable medium. The computer-readable medium (also referred to as computer-readable media) may include a computer storage medium which may be referred to as a non-transitory computer-readable medium. A non-transitory computer-readable medium may exclude transitory signals. Computer-readable media may include both computer storage media and communication media including any medium that may facilitate transfer of a computer program from one place to another. A storage medium may be any available media that can be accessed by a computer. By way of example, and not limitation, such computer-readable media can comprise RAM, ROM, electrically erasable programmable ROM ("EEPROM"), compact disc read-only memory ("CD-ROM") or other optical disk storage, magnetic disk storage or other magnetic storage devices, or any other medium that can be used to store desired program code in the form of instructions or data structures and that can be accessed by a computer. Disk and disc, as used herein, may include compact disc ("CD"), laser disc, optical disc, digital versatile disc ("DVD"), floppy disk and Blu-ray disc, where disks usually reproduce data magnetically, while discs usually reproduce data optically with lasers. Combinations of the above may also be included within the scope of computer-readable media.

The previous description is provided to enable any person skilled in the art to practice the various aspects described herein. Various modifications to these aspects will be readily apparent to those skilled in the art, and the generic principles defined herein may be applied to other aspects. Thus, the claims are not intended to be limited to the aspects shown herein, but is to be accorded the full scope consistent with the language claims, wherein reference to an element in the singular is not intended to mean "one and only one" unless specifically so stated, but rather "one or more." The word "exemplary" is used herein to mean "serving as an example, instance, or illustration." Any aspect described herein as "exemplary" is not necessarily to be construed as preferred or advantageous over other aspects. Unless specifically stated otherwise, the term "some" refers to one or more. Combinations such as "at least one of A, B, or C," "one or more of A, B, or C," "at least one of A, B, and C," "one or more of A, B, and C," and "A, B, C, or any combination thereof" include any combination of A, B, and/or C, and may include multiples of A, multiples of B, or multiples of C. Specifically, combinations such as "at least one of A, B, or C," "one or more of A, B, or C," "at least one of A, B, and C," "one or more of A, B, and C," and "A, B, C, or any combination thereof" may be A only, B only, C only, A and B, A and C, B and C, or A and B and C, where any such combinations may contain one or more member or members of A, B, or C. All structural and functional equivalents to the elements of the various aspects described throughout this disclosure that are known or later come to be known to those of ordinary skill in the art are expressly incorporated herein by reference and are intended to be encompassed by the claims.

Moreover, nothing disclosed herein is intended to be dedicated to the public regardless of whether such disclosure is explicitly recited in the claims. The words "module," "mechanism," "element," "device," and the like may not be a substitute for the word "means." As such, no claim element is to be construed as a means plus function unless the element is expressly recited using the phrase "means for."

What is claimed is:

1. A method of operating an access control system, comprising:
    detecting whether a person has sanitized one or more body parts of the person;
    where the person has sanitized the one or more body parts, obtaining access credentials of the person by permitting user access to an input device of the access control system;
    where the person has not sanitized the one or more body parts, preventing obtaining of the access credentials of the person by preventing the user access to the input device of the access control system; and
    selectively unlocking or maintaining an application of a physical lock responsive to at least the access credentials and detecting that the person has sanitized the one or more body parts.

2. The method of claim 1, further comprising:
    sensing a presence of the person at an access control area; and
    dispensing, in response to detecting the presence of the person at the access control area, an amount of sanitizing liquid,
    wherein detecting whether the person has sanitized the one or more body parts comprises detecting whether the person has sanitized the one or more body parts using the sanitizing liquid.

3. The method of claim 1, further comprising:
    capturing the access credentials of the person;
    dispensing, in response to capturing the access credentials of the person, an amount of sanitizing liquid; and
    instructing a checkpoint controller of the access control system that controls the physical lock to remain in a locked state during a time period, the time period being configured according to a time duration needed to apply the sanitizing liquid.

4. The method of claim 1, further comprising:
    emitting ultraviolet light into a palm placement area,
    wherein detecting whether the person has sanitized the one or more body parts comprises detecting that the one or more body parts have remained at the palm placement area during a time period exceeding a minimum duration.

5. The method of claim 1, wherein detecting whether the person has sanitized the one or more body parts comprises:
    receiving, from a sanitizing station, an indication that the person has sanitized the one or more body parts of the person.

6. The method of claim 1, wherein obtaining the access credentials comprises:
    capturing, via a scanning device of the access control system, the access credentials of the person, the scanning device being configured to capture at least one of an access code, a fingerprint, a palm print, a facial image, a vocal input, an iris scan, a heartbeat scan, an identity card barcode, a quick response ("QR") code, and identification information from a device of the person.

7. The method of claim 1, further comprising:
    instructing, in response to detecting that the person has not sanitized the one or more body parts, a checkpoint controller of the access control system that controls the physical lock to remain in a locked state.

8. The method of claim 1, wherein preventing obtaining of the access credentials of the person includes disabling an input device of the access control system where the person has not sanitized the one or more body parts.

9. An apparatus of an access control system, comprising:
    a non-transitory memory storing computer-executable instructions; and
    a processor communicatively coupled with the non-transitory memory and configured to execute the computer-executable instructions to:
        detect whether a person has sanitized one or more body parts of the person;
        where the person has sanitized the one or more body parts, obtain access credentials of the person by permitting user access to an input device of the access control system;
        where the person has not sanitized the one or more body parts, prevent obtaining of the access credentials of the person by preventing the user access to the input device of the access control system; and
        selectively unlocking or maintaining an application of a physical lock responsive to at least the access credentials and detecting that the person has sanitized the one or more body parts.

10. The apparatus of claim 9, wherein the processor is configured to execute further computer-executable instructions to:
    sense a presence of the person at an access control area; and
    dispense, in response to detecting the presence of the person at the access control area, an amount of sanitizing liquid,
    wherein to detect whether the person has sanitized the one or more body parts comprises to detect whether the person has sanitized the one or more body parts using the sanitizing liquid.

11. The apparatus of claim 9, wherein the processor is configured to execute further computer-executable instructions to:
    capture the access credentials of the person;
    dispense, in response to capturing the access credentials of the person, an amount of sanitizing liquid; and
    instruct a checkpoint controller of the access control system that controls the physical lock to remain in a locked state during a time period, the time period being configured according to a time duration needed to apply the sanitizing liquid.

12. The apparatus of claim 9, wherein the processor is configured to execute further computer-executable instructions to:
    emit ultraviolet light into a palm placement area,
    wherein to detect whether the person has sanitized the one or more body parts comprises to detect that the one or more body parts have remained at the palm placement area during a time period exceeding a minimum duration.

13. The apparatus of claim 9, wherein to detect whether the person has sanitized the one or more body parts comprises to:
receive, from a sanitizing station, an indication that the person has sanitized the one or more body parts of the person.

14. The apparatus of claim 9, further comprising:
a scanning device configured to capture at least one of an access code, a fingerprint, a palm print, a facial image, a vocal input, an iris scan, a heartbeat scan, an identity card barcode, a quick response ("QR") code, and identification information from a device of the person,
wherein to obtain the access credentials comprises to capture, via a scanning device of the access control system, the access credentials of the person.

15. The apparatus of claim 9, wherein the processor is configured to execute further computer-executable instructions to:
instruct, in response to detecting that the person has not sanitized the one or more body parts, a checkpoint controller of the access control system that controls the physical lock to remain in a locked state.

16. A non-transitory computer-readable medium storing computer-executable instructions for operating an access control system, executable by a processor to:
detect whether a person has sanitized one or more body parts of the person;
where the person has sanitized the one or more body parts, obtain access credentials of the person by permitting user access to an input device of the access control system;
where the person has not sanitized the one or more body parts, prevent obtaining of the access credentials of the person by preventing the user access to the input device of the access control system; and
selectively unlock or maintain an application of a physical lock responsive to at least the access credentials and detecting that the person has sanitized the one or more body parts.

17. The non-transitory computer-readable medium of claim 16, wherein the non-transitory computer-readable medium stores further computer-executable instructions, executable by the processor to:
sense a presence of the person at an access control area; and
dispense, in response to detecting the presence of the person at the access control area, an amount of sanitizing liquid,
wherein to detect whether the person has sanitized the one or more body parts comprises to detect whether the person has sanitized the one or more body parts using the sanitizing liquid.

18. The non-transitory computer-readable medium of claim 16, wherein the non-transitory computer-readable medium stores further computer-executable instructions, executable by the processor to:
capture the access credentials of the person;
dispense, in response to capturing the access credentials of the person, an amount of sanitizing liquid; and
instruct a checkpoint controller of the access control system that controls the physical lock to remain in a locked state during a time period, the time period being configured according to a time duration needed to apply the sanitizing liquid.

19. The non-transitory computer-readable medium of claim 16, wherein the non-transitory computer-readable medium stores further computer-executable instructions, executable by the processor to:
emit ultraviolet light into a palm placement area,
wherein to detect whether the person has sanitized the one or more body parts comprises to detect that the one or more body parts have remained at the palm placement area during a time period exceeding a minimum duration.

20. The non-transitory computer-readable medium of claim 16, wherein computer-executable instructions to detect whether the person has sanitized the one or more body parts comprises further computer-executable instructions to:
receive, from a sanitizing station, an indication that the person has sanitized the one or more body parts of the person.

21. The non-transitory computer-readable medium of claim 16, wherein the non-transitory computer-readable medium stores further computer-executable instructions, executable by the processor to:
instruct, in response to detecting that the person has not sanitized the one or more body parts, a checkpoint controller of the access control system that controls the physical lock to remain in a locked state.

* * * * *